United States Patent [19]
Reinsch

[11] 3,935,869
[45] Feb. 3, 1976

[54] APPLICATOR DRIVE UNIT

[76] Inventor: Arnold O. Winfried Reinsch, 13170 Carousel Lane, Del Mar, Calif. 92014

[22] Filed: June 5, 1974

[21] Appl. No.: 476,717

Related U.S. Application Data

[63] Continuation-in-part of Ser. No. 330,694, Feb. 6, 1973, abandoned.

[52] U.S. Cl. ................................ 132/9; 132/85
[51] Int. Cl.² ............................... A45D 24/16
[58] Field of Search ............. 132/9, 85, 141, 114; 15/22; 128/32; 310/15, 51; 248/18

[56] References Cited
UNITED STATES PATENTS

| | | | |
|---|---|---|---|
| 1,686,936 | 10/1928 | Simpson | 132/114 |
| 2,305,969 | 12/1942 | Larson | 132/141 |
| 3,233,265 | 2/1966 | Hartmann | 15/22 |
| 3,278,963 | 10/1966 | Bond | 15/22 |
| 3,538,617 | 11/1970 | Walters | 132/9 |

*Primary Examiner*—G. E. McNeill

[57] ABSTRACT

A drive unit operates an applicator for massage, brushing, cleaning, and the like. The drive unit moves the applicator in a unique translatory motion in which the plane of the applicator maintains an unchanging orientation relative to the drive unit and has a lapping or stroking action on the body of the user which is effectively unidirectional at the body surface. This motion is very effective for many applications in which reciprocating or rotational movement is less appropriate, such as stimulating the blood circulation, brushing the teeth, and hair grooming, and different applicators as well as drive units are provided which are particularly adapted to accomplish these functions.

6 Claims, 10 Drawing Figures

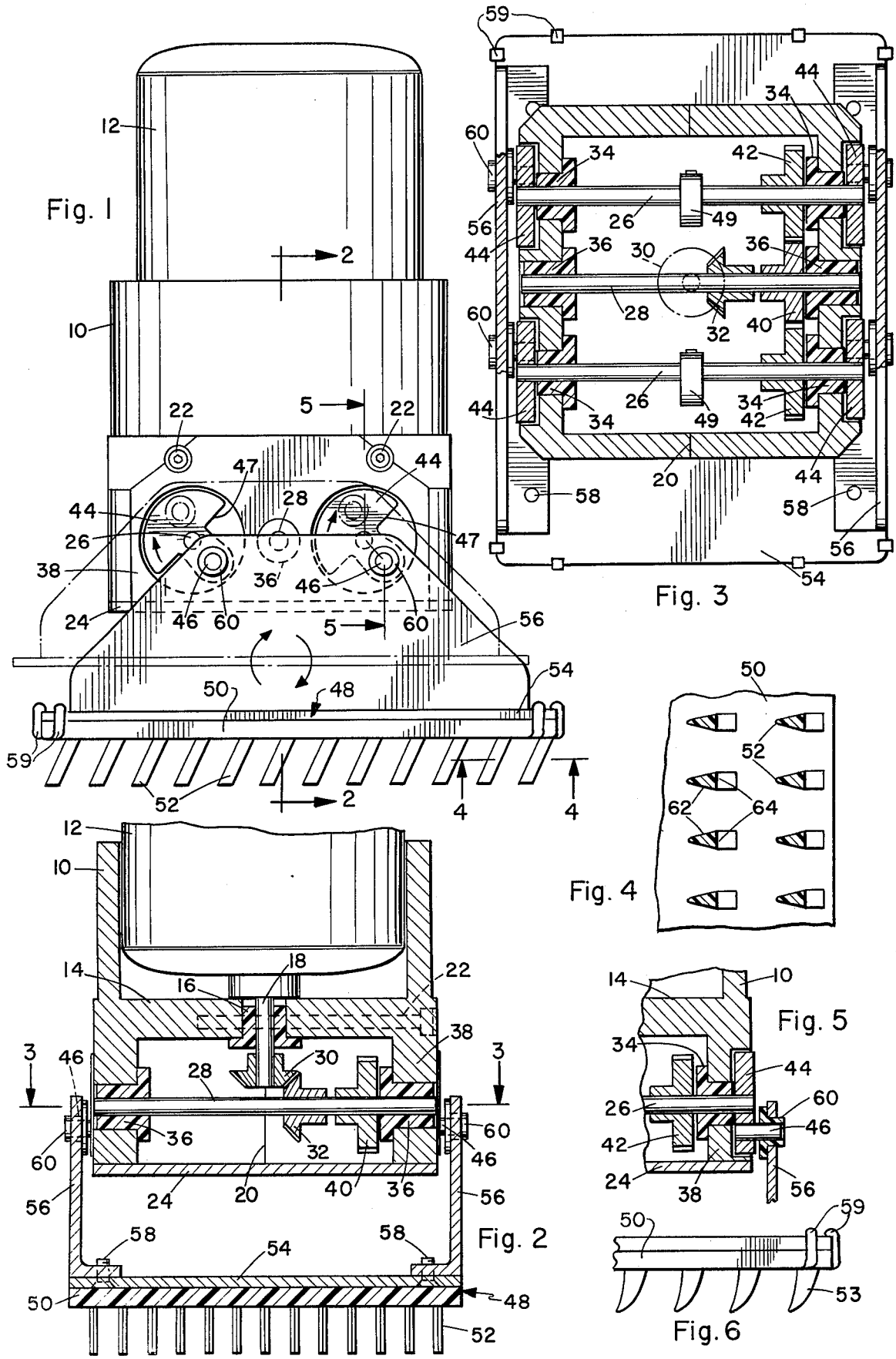

APPLICATOR DRIVE UNIT

BACKGROUND OF THE INVENTION

This application is a Continuation - In - Part of an application filed Feb. 6, 1973 titled "Applicator With Effective Translatory-Vibratory Drive Unit" having Ser. No. 330,694 now abandoned.

Many types of vibrating machines, including hand-held models have been developed and marketed. Nearly all of these prior art devices include an electric motor and most of them include an eccentrically driven element of considerable mass to provide the vibratory motion, usually to the whole assembly in the case of hand-held devices. Different pads or applicators have been employed previously, some for body massage, others for scalp massage, shampooing of the hair, or brushing the teeth. But the design of the vibrator is usually based on a rotating imbalance or a vibrating mass that imparts its vibration to the massager. A circular motion is caused by a rotating imbalance and a back and forth type of vibration by a simple oscillation of a mass. None of these prior art devices has a primary direction of movement at the contact surface. Consequently, there is a need for a drive unit which drives a massage or brushing applicator with an effectively unidirectional lapping motion.

SUMMARY OF THE INVENTION

The invention is a hand-held machine which meets the abovementioned need and comprises a casing functioning as a handle and motor holder, the motor being preferably a variable speed electric motor with transmission means including one or more shafts each carrying a pair of opposed eccentrics which drive an exchangeable applicator or pad. The applicator is driven in such a manner that during the part of the operative cycle in which the maximum pressure is exerted against the body of the user the applicator is moving primarily in one direction. In one general embodiment of the invention designed for massage and hair grooming several interchangeable applicators may be provided which include a massage pad, a hair brush, and an applicator having specially designed projections which effectively clean the hair and massage the scalp. In another embodiment the drive unit is modified for use in an electric tooth brush and the applicator is provided with bristles, the movement of the brush portion being the unidirectional motion described above which has long been endorsed by the dental profession as the optimal brushing technique but has not been incorporated in any of the units currently on the market.

BRIEF DESCRIPTION OF THE DRAWINGS

FIG. 1 is a side elevation view of the vibratory drive unit;

FIG. 2 is a sectional view taken on line 2—2 of FIG. 1;

FIG. 3 is a sectional view taken on line 3—3 of FIG. 2;

FIG. 4 is an enlarged sectional view taken on line 4—4 of FIG. 1;

FIG. 5 is a sectional view taken on line 5—5 of FIG. 1;

FIG. 6 is a view of an alternative applicator;

DETAILED DESCRIPTION OF THE PREFERRED EMBODIMENTS

Figure 7:
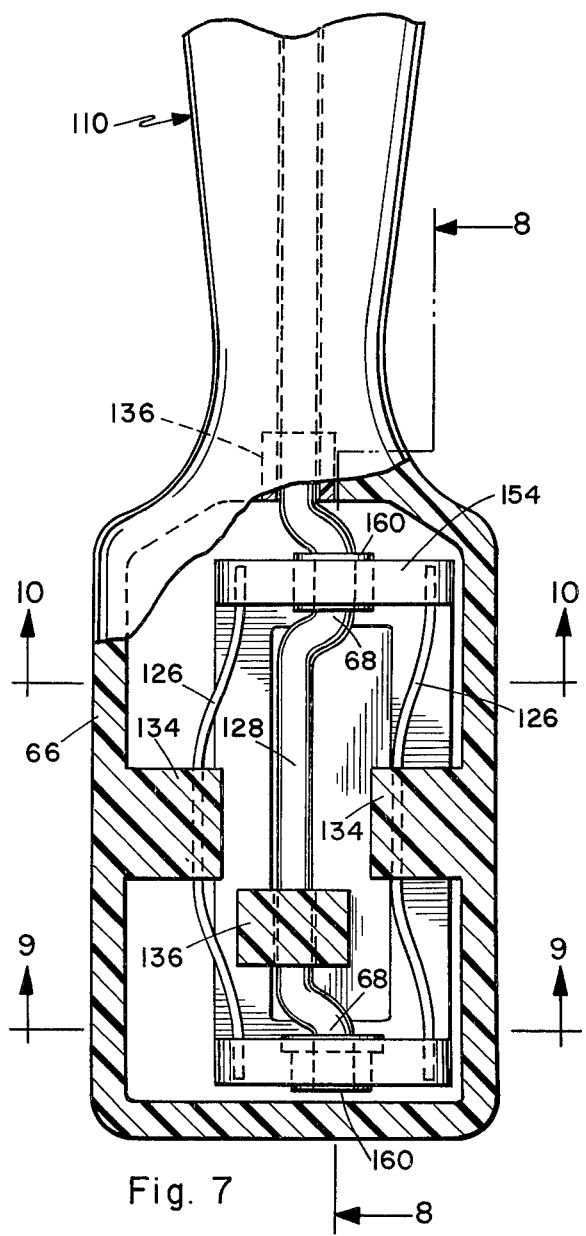
FIG. 7 is a top plan view, partially cut away, of a tooth brush adaptation of the mechanism.
Figure 8:
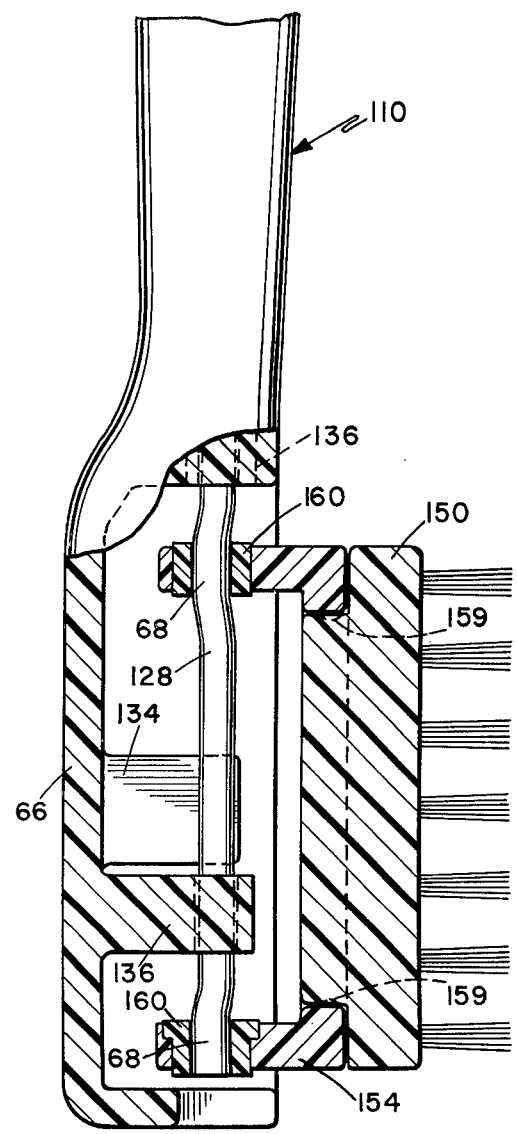
FIG. 8 is a sectional view taken on line 8—8 of FIG. 7.
Figure 9:
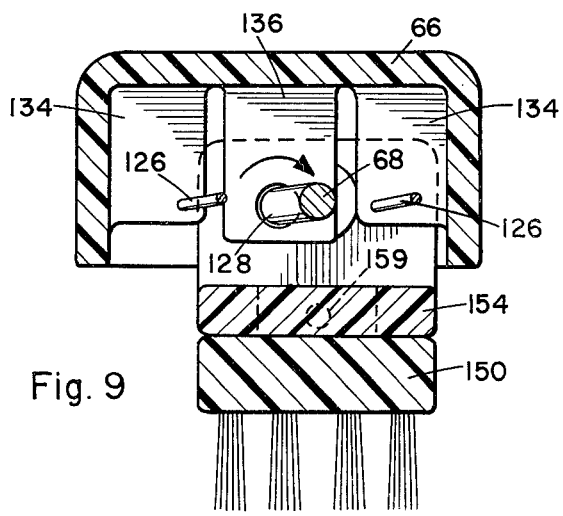
FIG. 9 is a sectional view taken on line 9—9 of FIG. 7.
Figure 10:
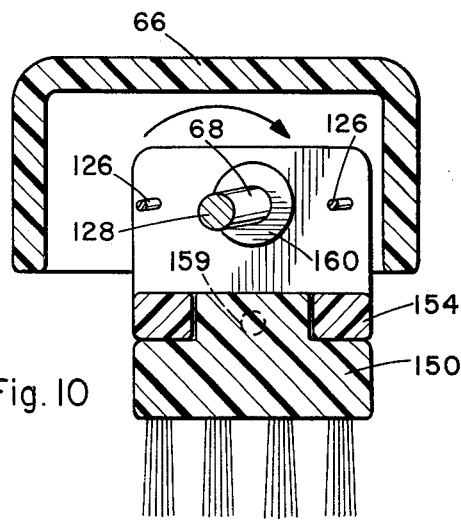
FIG. 10 is a sectional view taken on line 10—10 of FIG. 7.

Although the item can be constructed in different forms while retaining the principal features of a unique applicator movement with cooperative interchangeable applicators, two representative forms are illustrated, FIGS. 1 through 6 being a massage and grooming embodiment and FIGS. 7 through 10 indicating a tooth brush variation. Referring first to the first embodiment in FIGS. 1 through 6, the casing 10 is a cylindrical shell dimensioned for snug reception of one end of an electric motor 12, preferably of variable speed type and dimensioned to be hand-held so that it may function, if that is desired, as a handle for the device.

The inner end of the casing 10 has a wall 14 which supports a bearing 16 for the drive shaft 18 of the motor and for ease of assembly the casing 10 may be made in two complementary shell parts which abutt along a line indicated at 20 in FIGS. 2 and 3, the two shells being held together by bolts 22 adjacent to the bearing 16 and by end plate 24. This construction also facilitates mounting of two parallel cross shafts 26, one on either side of a secondary drive shaft 28 driven by miter gears 30, 32 on the motor drive shaft 18 and on the secondary drive shaft 28, respectively.

The cross shafts 26 have bearings 34 and the secondary drive shaft has bearings 36, all mounted in the extending portions 38 of said complementary shell portions of the casing 10 as already described. A drive gear 40 on the secondary drive shaft 28 meshes with gears 42 on each of the cross shafts 26.

To complete the transmission means each cross shaft has at each end a disc identified at 44, with an eccentrically mounted journal 46 and these journals must be in phase so that the applicator mounting bracket, generally indicated at 48, will be operated with the required lapping motion. The discs 44 are eccentrically weighted as by being relieved or cut away as at 47 and additionally a counterweight indicated at 49 can be carried by the shafts 26 to offset the mass of the applicators and mounting bracket. The illustrated applicator comprises a generally planar backing 50 with hair engaging projections 52, hereinafter described more fully, and the mounting bracket 48 comprises a plate 54 which will ordinarily be metal and wall structure 56, shown as two parallel opposed angles secured to the plate 54 by screws 58 and carrying bearings 60 in which the eccentric journals 46 are received. The applicator is removably engaged on the plate 54 by slightly resilient detents 59 which snap over the plate in conventional fashion, it being understood that any suitable quick-release attachment means could be used. It will thus be made clear that the applicator is made to move with said lapping motion, each part of the applicator moving in a circle with the effective radius of the eccentric, that is, with a translatory component which may be thought of as horizontal in the representation in FIG. 1, the effective portion of the translatory component being as to the left in that figure, the following portion of the movement being a withdrawal, upwardly in that figure, and the reverse translatory portion of the movement being considerably less significant in the actual functional operation of the machine.

This lapping movement is necessarily related with the configuration of the hair-engaging projections 52 of the applicator illustrated. These projections have a cross-sectional shape defining a tapered or streamlined forward face 62 and a cavitation-inducing rear face 64 flat or concave. One very simple configuration is that represented in FIG. 4 wherein the streamlined face is continued to the edges of the cavitation inducing face which latter is shown as a simple flat surface. The projections may be staggered if desired. It is preferable that the projections 52 shall be somewhat flexible and that these projections be inclined relative to the backing 50. It is also preferable that the inclination be in the direction of the effective, or outer translatory movement, that is, to the left as represented in FIG. 1. The projections may be longitudinally arcuate when a more gentle action is required as indicated at 53 in FIG. 6.

The device has a dual function in massaging the scalp in a particularly effective, and agreeable manner and in cleaning the hair. The motion imparted to the hair by the applicator 48 is transmitted to the scalp producing a gentle overall massage in a natural way without necessarily touching the scalp. The rapid effective translatory movement of the projections 52 is related functionally with the cavitation of particular matter onto face 64 where it remains and is withdrawn in situ with the applicator when the user removes the machine from his or her hair. This matter is easily removed from the applicator after use and the applicator can be used repeatedly and indefinitely.

The drive unit, by reason of its effectively unidirectional translatory component in the applicator, is ideally suited to blood circulation therapy, that is, stimulation of circulation of blood in or close to the skin. This also applies to the stimulation of the medically accepted tree flow pattern, up the right side and down the left side of the body. An applicator such as those illustrated in the drawing may be used for grooming or the applicator may be varied according to the dictates of comfort and preference. It is contemplated that applicators having massage pads, bristles for brushing the hair, or possibly a plurality of rollers to reduce sliding friction on the skin during massage be provided for use in the alternative, the clip-on design of the applicators enabling the rapid exchange of the various applicator types and the effective unidirectional motion being advantageous in all applicators.

Reference is now made to the embodiment of the invention modified for use on a toothbrush illustrated in FIGS. 7 through 10, in which elements which are counterparts to the first embodiment are similarly numbered but in the one hundred series. The casing 110 is elongated and includes a shank or handle portion (not shown) typical of electric toothbrushes. The operative end 66 of the casing is dimensioned to fit within the mouth and is provided with a pair of bearing members 136 in which is journalled a shaft 128. The shaft extends from a conventional electric motor in the handle (not shown) and is provided with a pair of eccentric crank portions 68 which carry a toothbrush mounting bracket 154 which is preferably journalled to the cranks through two crank bearings 160.

In order to substantially preserve the desired translational motion, a pair of resilient rods 126 are centrally captured in a pair of opposed supports 134 which are molded integrally with the end 66 of the casing. The ends of the rods are engaged by the brush mounting bracket 154 as shown such that each rod exerts a restraining force on the bracket which increases with the amount of deformity experienced by the rod so that the opposite sides have a tendency to be equally displaced in any given direction by the shaft 128, thereby retaining the translatory motion.

The variation in the transmission means in the second embodiment is suggested by the space limitations associated with an electric toothbrush as opposed to the larger massage unit. However, the single shaft design could clearly be used as an alternative in the first embodiment as well as the toothbrush. It should also be noted that the resilient rods 126 could be replaced with other restraining means, the crucial feature of the restraining means being their ability to bias the opposite sides of the mounting 154 toward the center of their circular motion during all phases of the operating cycle.

Mounted in the brush mounting bracket 154 is an applicator in the form of a brush element 150 which is preferably releasible for purposes of cleaning and exchange and is retained on the mounting by detents 159 which seat in appropriate sockets on the brush elements. Any other convenient releasible mounting means could be used.

One feature which should be present in the second embodiment of the invention but not necessarily in the first is reverse capability of the motor. This is desirable because otherwise the desired brushing motion, which is away from the gums, would be possible for only half of the tooth surfaces to be cleaned. The need for reversability could be obviated by the use of two brush mechanisms mounted side-by-side in the casing and having opposite motions such that the effective directions of translation would be toward one another. This arrangement would have the added advantage that one side of both the upper and lower rows of teeth could be brushed simultaneously. A single shaft comparable to the shaft 128 could be used to drive both brushes, with a simple gear mechanism to achieve appropriate motion.

I claim:
1. An applicator drive unit for treating a surface comprising:
   a casing;
   a pair of generally parallel rods mounted in said casing, each of said rods having a pair of eccentric portions;
   a mounting bracket mounted to the eccentric portions of said rods;
   an applicator element attached to said mounting bracket;
   a motor operatively mounted in said casing;
   power transmission means operatively connecting said motor and mounting bracket for driving said mounting bracket circularly on the eccentric portions of said rods such that all portions of the applicator element have substantially translational circular motion whereby the orientation of the applicator element with respect to the casing is maintained substantially constant and the applicator has a lapping action in use to produce substantially one effective direction of motion relative to the surface treated.
2. Structure according to claim 1 wherein said rods comprise rigid shafts rotationally mounted in said bracket, said mounting bracket being journalled on said eccentric portions, and including means restricting said shafts to in-phase motion whereby said applicator is restricted to substantially translational motion.

3. Structure according to claim 1 wherein said applicator element has a plurality of substantially parallel hair-engaging elements projecting therefrom, and with respect to said one effective direction of motion, each of said hair-engaging elements has a streamlined portion on the leading side and a cavitation-inducing portion on the trailing side to harbour particulate foreign matter extracted from the hair and scalp.

4. Structure according to claim 1 wherein said rods are resilient and centrally mounted in said casing, said bracket being engaged on the ends of said rods whereby said rods are attached toward the individual centers of the circular motion undergone by said mounting bracket portions.

5. Structure according to claim 4 and including a drive shaft generally parallel to and between said rods and having eccentric portions engaging said bracket.

6. Structure according to claim 4 wherein said casing has a portion thereof dimensioned to fit in the human mouth, said mounting bracket is disposed in said casing portion, and said applicator element is provided with bristles adapted to tooth brushing.

* * * * *